United States Patent
Bombarrdelli et al.

(10) Patent No.: US 8,247,005 B2
(45) Date of Patent: Aug. 21, 2012

(54) **PROCESS FOR COSMETIC TREATMENT USING FERUTININE FROM *FERULA* GENUS PLANTS**

(75) Inventors: Ezio Bombarrdelli, Groppello Cairoli (IT); Gabriele Fontana, Milan (IT); Aldo Cristoni, Milan (IT); Enrico Mercalli, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 13/324,339

(22) Filed: Dec. 13, 2011

(65) Prior Publication Data

US 2012/0095094 A1 Apr. 19, 2012

Related U.S. Application Data

(60) Division of application No. 12/816,671, filed on Jun. 16, 2010, now Pat. No. 8,101,215, which is a continuation of application No. 12/058,776, filed on Mar. 31, 2008, now abandoned, which is a division of application No. 10/551,772, filed as application No. PCT/EP2004/003055 on Mar. 23, 2004, now Pat. No. 7,371,886.

(30) Foreign Application Priority Data

Apr. 4, 2003 (IT) .............................. MI2003A0661

(51) Int. Cl.
*A01N 65/00* (2009.01)
(52) U.S. Cl. ....................................... 424/725
(58) Field of Classification Search .................. None
See application file for complete search history.

(56) References Cited

U.S. PATENT DOCUMENTS 5,952,373 A 9/1999 Lanzendorfer et al.
6,623,768 B1 9/2003 Naguib
2002/0034557 A1 3/2002 Crosby et al.

FOREIGN PATENT DOCUMENTS

CH 672 251 11/1989
GB 1 604 225 12/1981

OTHER PUBLICATIONS

Tamemoto Kimiko et al: "Sesquiterpenoids from the fruits of *Ferula kuhistanica* and antibacterial activity of the constituents of *F. kuhistanica*" Phytochemistry (Oxford), vol. 58, No. 5, Nov. 2001, pp. 763-767, XP004310053 ISSN: 0031-9422 p. 765, paragraph 5; table 3; compound 4.
Galal A M et al; "Daucane sesquiterpenes from *Ferula hermonis*." Journal of Natural Products. Mar. 2001, vol. 64, No. 3, Mar. 2001; pp. 399-400, XP002290428 ISSN: 0163-3864 abstract; compound 3.
Patent Abstracts of Japan vol. 2000, No. 24, May 11, 2001 & JP 2001 206819 A (Shansho Seiyaku Co LTD), Jul. 31, 2001 abstract.
Tamemoto et al., Sequiterpenoids from the fruits of *Ferula kuhistanica* and antibacterial activity of the constituents of *F. kuhistanica*, Phytochem., vol. 58, pp. 763-767 (2001).
Tolstikov et al., "Prostanoids LVIII—New a.w.-Noranoalogs of prostaglandins from ferutinol," J. Org. Chem. USSR, vol. 28, No. 10, pp. 2081-2090 (Oct. 1992).
The Third Party Observation issued in the correponding EP application on Feb. 7, 2009.

*Primary Examiner* — Michael Meller
(74) *Attorney, Agent, or Firm* — Young & Thompson

(57) ABSTRACT

The invention relates to a process for cosmetic treatment, including the reduction of superficial and deep wrinkles, using ferutinine from *Ferula* spp extracts.

4 Claims, No Drawings

PROCESS FOR COSMETIC TREATMENT USING FERUTININE FROM *FERULA* GENUS PLANTS

CROSS REFERENCE TO RELATED APPLICATIONS

This application is a division of co-pending application Ser. No. 12/816,671 filed on Jun. 16, 2010; which is a continuation of application Ser. No. 12/058,776 filed on Mar. 31, 2008; which is a division of application Ser. No. 10/551,772, now U.S. Pat. No. 7,371,886; which is the 35 U.S.C. §371 national stage of International PCT/EP2004/003055 filed on Mar. 23, 2004, which claims priority to Italian Application No. MI2003A000661 filed on Apr. 4, 2003. The entire contents of each of the above-identified applications are hereby incorporated by reference.

FIELD OF THE INVENTION

The present invention relates to vegetable extracts from *Ferula* spp and to a process for isolating ferutinine from said extracts.

BACKGROUND OF THE INVENTION

Numerous *Ferula* genus plants contain terpenes with estrogenic activity, known also as phytoestrogens, i.e. substances which regulate hormonal functions and are apparently a valid alternative to the use of synthetic hormones in the treatment of pre-menstrual syndrome and disorders related to menopause and aging. Extracts of some types of *Ferula* were used in ancient times as contraceptives and in the treatment of impotence and menopausal disorders. Recently, alcoholic extracts from *Ferula asafoetida L.* have been disclosed (WO 0230438) as anticancer drugs.

The most abundant compounds in *Ferula* genus plants are derivatives of jaeschkenadiol (II):

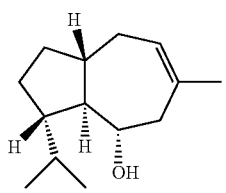

(II)

in particular daucane esters having the general formula (I)

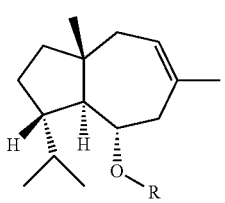

(I)

Daucane esters are known compounds and are for example disclosed in Phytochemistry, vol. 37, no 3, pages 597-623, 1994. In the formula (I) R is a straight or branched, saturated or unsaturated aliphatic acyl residue, or an optionally substituted aromatic acyl residue. Examples of R groups are isovaleroyl, angeloyl, benzoyl, p-hydroxybenzyl, veratroyl or cinnammoyl.

Daucane esters from *Ferula* spp are estrogen modulators similar to SERMs (selective estrogen receptor modulators); among them, ferutinine (Ia) shows marked estrogenic activity, whereas the others have a rather mild activity.

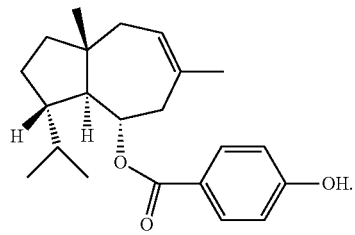

(Ia)

In particular, ferutinine is an estrogen receptor alpha agonist (ER) and an estrogen receptor beta agonist/antagonist (ER). It has also been shown that ferutinine has higher binding to estrogen receptors than tamoxifen.

There is therefore the need to obtain ferutinine-enriched extracts or optimise the extraction of ferutinine in the pure form from plant materials containing its precursors.

A process comprising the hydrolysis of a daucane esters whole extract to give crude jaeschkenadiol and the subsequent re-esterification of jaeschkenadiol with suitably protected p-hydroxybenzoic acid, for example with p-acetoxybenzoic acid, is known from the literature (J. Org. Chem. USSR (Engl. Transl.); EN; 28; 10; 1992; 1666-1673). Nevertheless, this process gives rather poor yields (about 45%), mainly due to competitive transesterification reactions.

DETAILED DISCLOSURE OF THE INVENTION

It has now been found that the use of p-pivaloyloxybenzoic acid as esterifying agent allows to avoid competitive reactions responsible for low conversion yields.

Object of the present invention is therefore a process for the preparation of ferutinine (Ia)

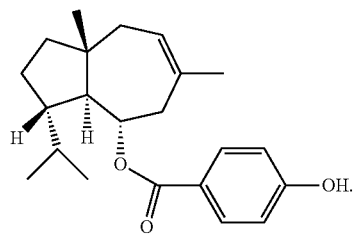

(Ia)

which comprises the following steps:
a) extraction of daucane esters from *Ferula* spp;
b) basic hydrolysis of daucane esters to give jaeschkenadiol (II)

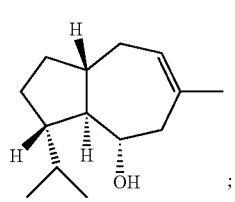

(II)

c) esterification of jaeschkenadiol (II) with p-pivaloyloxybenzoic acid (III)

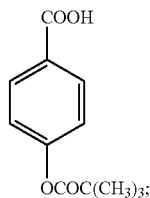
(III)

to give p-pivaloyloxyferutinine (IV)

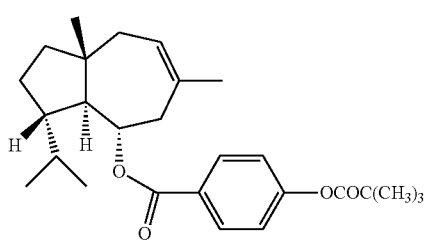
(IV)

d) hydrolysis of p-pivaloyloxyferutinine (IV) to ferutinine.

"Daucane esters" means compounds of the general formula (I) as defined above; said esters can be obtained by extraction of the rhizomes or aerial parts of *Ferula* spp, preferably *Ferula communis* and *Ferula hermonis*, with conventional methods, for example by extraction with lower alcohols. Starting from *Ferula hermonis* rhizomes containing ferutinine and jaeschkenadiol benzoic ester (not easily separable by chromatography) in 1:1 ratio, pure ferutinine can be isolated by extracting the roots with methanol, treating the extract with 5% KOH and back-extracting the saponified extract with aliphatic hydrocarbons, ethers, esters or chlorinated solvents.

Alternatively, daucane esters can be obtained by extraction with supercritical $CO_2$ at temperatures ranging from 35 to 65° C., preferably at 45° C., and pressures ranging from 200 to 260 bar, preferably at 245 bar. In the separator (or in the separators) the temperature ranges from 25 to 45° C. and the pressure is of about 50 bar. In these experimental conditions gummy materials, which make the recovery of the desired compounds difficult, are not extracted. The residue can be directly submitted to saponification according to what reported in the examples.

Jaeschkenadiol is esterified with p-pivaloylossibenzoic acid and treated, in the same reaction solvent, with a base, preferably a primary amine, more preferably ethylenediamine, to give pure ferutinine. According to a preferred embodiment of the invention, steps c) and d) are conveniently carried out in sequence without recovery of intermediate p-pivaloyloxyferutinine.

A further object of the present invention is the cosmetic and dermatological use of ferutinine, p-pivaloyloxyferutinine and extracts, of *Ferula* spp, preferably *Ferula communis* and *Ferula hermonis* extracts.

When applied on the skin, ferutinine and *Ferula* spp extracts surprisingly proved able to increase collagen biosynthesis and to exert a tonic, trophic and moisturizing action, thus giving firmness and elasticity. Moreover, they reduce sebum secretion and play a remarkable role in the control of hirsutism and face virilization. Therefore, compositions containing ferutinine or *Ferula* spp extracts can be used in the cosmetic or dermatological field for the treatment of superficial or deep wrinkles or other unaesthetisms, as well as for the treatment of various acne and seborrhea forms.

Ferutinine and *Ferula* spp extracts can be formulated in the form of creams, gels and lotions in admixture with conventional excipients, for example those described in Remington's Pharmaceutical Sciences Handbook, XVII ed., Mack Pub., N.Y., U.S.A., preferably in the presence of soy lecithin or phospholipids, such as lauroylphosphatidylcoline and myristoylphosphatidilcoline, which can be incorporated in water/oil and oil/water emulsions or in transdermal plasters.

The following examples illustrate the invention in greater detail.

EXAMPLES

Example 1

Isolation of jaeschkenadiol from *Ferula hermonis* Roots 250 g of finely ground *Ferula hermonis* roots (particle size distribution: 2 mm) are extracted by percolation with 1 l MeOH. After maceration for two days and percolation of the solvent, the operation is repeated (4×1 l), to obtain 112.2 g of methanol extract (45%). Drug exhaustion is monitored by TLC (petroleum ether/EtOAc 8/2, ferutinine $R_f$: 0.14).

The methanol extract is refluxed with 513 ml of a 10% KOH methanol solution. After 1 h, TLC analysis (petroleum ether-EtOAc 8/2, ferutinine $R_f$: 0.14; $R_f$ jaeschkenadiol: 0.31) shows that the reaction is complete. After cooling, the reaction mixture is diluted with water (500 ml) and extracted with petroleum ether (4×500 ml). The combined petroleum ether phases are washed with brine, dried and evaporated. The resulting semicrystalline residue is washed with cold petroleum ether (refrigerator temperature) to obtain 7.5 g of crystalline jaeschkenadiol. The mother liquors are purified by chromatography (50 g silica gel, petroleum-ether-EtOAc 95:5), to obtain -bisabolol (870 mg), a mixture of -bisabolol and jaeschkenadiol, and pure jaeschkenadiol (3.4 g after crystallization). The mixture of jaeschkenadiol and -bisabolol is pooled with the mother liquor and chromatographed (50 g silica gel, petroleum ether-EtOAc 95:5), to obtain 1.95 g of crystalline jaeschkenadiol (overall yield: 12.85 g, 5.1%).

The compound has the following chemical-physical and spectroscopic properties:

IR spectrum (KBr, $cm^{-1}$): 3339, 2965, 2905, 2875, 1470, 1375, 1047, 968, 858

Mass spectrum (C.I.)
$M^+ + 1 - H_2O = 221$; $M^+ + 1 - 2H_2O = 203$ $^1$H NMR spectrum (300 MHZ, $CDCl_3$): H9 5.43 m, H2 3.9 m, H14 1.78 s, H15 1.00 s, H12 0.95 d J 4.98, H13 0.91 d J 5.13.

Example 2

Isolation of jaeschkenadiol from *Ferula communis* Roots 250 g of finely ground *Ferula communis* roots (particle size distribution: 2 mm) are extracted by percolation using 1 l MeOH. After maceration for two days and percolation of the solvent, the operation is repeated (4×1 l); the methanol extracts are concentrated to a volume equal to the weight of the ground roots and the extract is added with 10% KOH (10 ml). The alkaline solution is refluxed for 2 hours, then cooled and back-extracted three times with 200 ml of n-hexane. Drug exhaustion is monitored by TLC (petroleum ether/EtOAc 8/2).

The combined hexane phases are washed with brine, dried and evaporated. The resulting semicrystalline residue is washed with cold petroleum ether (refrigerator temperature), to obtain 3.5 g of crystalline jaeschkenadiol. The mother liquor is purified according to example 1. Yield: 0.8 g of jaeschkenadiol having the same chemical-physical properties as that of example 1.

Example 3

Isolation of jaeschkenadiol from *Ferula communis* Aerial Parts 1 kg of finely ground *Ferula communis* aerial parts are extracted with carbon dioxide at 45° C. and 245 bar in an apparatus for extraction with supercritical gases. In the separator (or in the separators) temperature ranges from 25 to 45° C. and pressure is of about 50 bar. In these conditions gummy materials that make it difficult to recover the desired compounds are not extracted. The residue, which contains only lipophilic compounds and water, is taken up with methanol and treated with bases to hydrolyse jaeschkenadiol esters, as reported in examples 1 and 2. After purification, 5.1 g of pure compound having the same characteristics of the product of example 1 is obtained.

Example 4

Synthesis of p-pivaloyloxybenzoic Acid

4-Hydroxybenzoic acid (114.5 g, 829 mmol) is dissolved under stirring in pyridine (1.15 l), cooling to T<5° C. on an ice bath. The resulting solution is added with 4-dimethylaminopyridine (DMAP, 0.3 equivalents, 248.8 mmol, 30.4 g) and pivaloyl chloride (3 equivalents, 2.487 mol, 300 g, 293.6 ml). The solution is allowed to warm up to room temperature and left under stirring for 2 h, then added with water (2.29 l) (exothermic reaction: cool the solution in an ice bath) and left under stirring for further 3 h.

The solution is poured into a separatory funnel and extracted with $CH_2Cl_2$ (3×750 ml). The combined methylene chloride phases are washed with 2 M $H_2SO_4$ (4×750 ml) and a saturated NaCl solution (1×1150 ml), then dried over $Na_2SO_4$ (60 g).

The solution is filtered through paper filter and the solvent is evaporated off under vacuum to obtain a residue which is triturated with petroleum ether at 30°-50° (3×400 ml), filtered by suction and dried under vacuum in a static dryer at 45° C. for 15 h. 130.5 g of product with the following spectroscopic characteristics is obtained.

IR spectrum (KBr, $cm^{-1}$): 3680, 2978, 2361, 1753, 1686, 1603, 1427, 1289, 1204, 1163, 1103.

Mass spectrum (C.I.): $M^+ +1 = 223$ $^1$H NMR spectrum (300 MHZ, D-DMSO) H3=7 8.00 d J=8.48, H4=6 7.23 d J=8.55, CH3 1.34 s.

Example 5

Synthesis of Ferutinine from Jaeschkenadiol

Jaeschkenadiol (100 g, 419.5 mmol) is dissolved under stirring at room temperature in $CH_2Cl_2$ (600 ml). The resulting solution is added with p-pivaloyloxybenzoic acid (1.4 equivalents, 587.3 mmol, 130.5 g) and DMAP (0.3 equivalents, 125.9 mmol, 15.4 g). The solution is left under stirring for 10 min. to complete reagents dissolution, then N,N'-dicyclohexylcarbodiimide (DCC, 1.8 equivalents, 755.1 mmol, 155.8 g) is added. The reaction is complete after 2 h.

The solution is concentrated to 2 volumes (200 ml) and diluted with 5 volumes of $CH_3CN$ (500 ml), thereafter the dicyclohexylurea precipitate is filtered off and washed with 5 more volumes of $CH_3CN$ (2×250 ml). The combined organic phases are poured into a separatory funnel, extracted with 10% w/v $Na_2CO_3$ (2×250 ml) and with a NaCl saturated solution (1×250 ml), then dried over $Na_2SO_4$ (100 g). $Na_2SO_4$ is filtered off and the solvent is evaporated under vacuum to give 360 g of compound (IV), having the following spectroscopic characteristics:

$^1$H NMR (300 MHZ, $CDCl_3$): 8.09 (d, J=9.0 Hz, H3'-H5'), 7.20 (d, J=8.7 Hz, H2'-H6'), 5.60 (brt, J=4.7 Hz, H9), 5.35 (td, J=10.4-2.9 Hz, H6), 2.58 (dd, J=13.1-10.9 Hz, H7b), 2.34 (dd, J=14.1-2.3 Hz, H7a), 2.07 (m, H10), 2.04 (d, J=2.7 Hz, H5), 1.97 (d, J=9.7 Hz, H2a), 1.89 (m, H11), 1.86 (s, H14), 1.63 (m, H2b), 1.57 (m, H3a), 1.41 (s, C(CH3)3), 1.30 (m, H3b), 1.14 (s, H15), 0.99 (d, J=6.9 Hz, H12), 0.89 (d, J=6.7 Hz, H13).

Compound (IV) is dissolved under stirring at room temperature in 2 l of $CH_2Cl_2$. The resulting solution is added with ethylenediamine (10 equivalents, 280 ml). After 3 h the reaction is complete. The solution is cooled to 0° C., poured into a separatory funnel, then washed with 3 M $H_2SO_4$ at 0° C. (2×750 ml, exothermic reaction) and a saturated NaCl solution (1×500 ml). The organic phase is dried over $Na_2SO_4$ (100 g), filtered and evaporated to dryness. The residue (230 g) is loaded onto a silica gel column (2.5 kg) equilibrated with 5.8 l of a hexane:AcOEt=9:1 mixture and eluted with 70 l of the same mixture. The product-containing fractions are pooled, the solvent is evaporated off under vacuum and the product is dried in a static dryer at 45° C. for 24 h.

139 g (92.4%) of product having the following spectroscopic characteristics is obtained:

IR spectrum (KBr, $cm^{-1}$): 3410, 1686, 1655, 1608, 1593, 1560, 1279, 1165, 1099, 771.

Mass spectrum (C.I.): $M^+ +1 - H_2O = 341$ $^1$H NMR spectrum (200 MHZ, $CDCl_3$): H3'=7' 7.94 d J=8, 4'=6' 6.88 d J=8, H9 5.56 m, H2 5.23 dt J=11, H14 1.80 brs, H15 1.10 s, H13 0.94 d J=6.5, H12 0.82 d J=6.5.

Example 6

Preparation of a *Ferula hermonis* Extract 1 kg of *Ferula hermonis* whole plant is extracted three times with 5 volumes of acetone. The combined acetone extracts are concentrated to 0.5 parts compared with the weight of the starting biomass and diluted with 2 parts of water. The aqueous solution is adjusted to pH 7.8 with diluted KOH, in the presence of hexane, under strong stirring. The hexane phase is discarded, the aqueous one is acidified to pH 5 and back-extracted with n-hexane. The hexane phase that contains ferutinine is concentrated to dryness to give 52 g of extract containing about 35% of ferutinine.

Example 7

Formulation Containing Ferutinine for the Treatment of Superficial Wrinkles Ferutinine is incorporated into a cream having the following composition:

| | |
|---|---|
| Ferutinine | 0.20 g |
| Carbomer 934 (Carbopol 934 P - Goodrich) | 0.60 g |
| Propylene glycol | 3.00 g |

-continued

| | |
|---|---|
| Imidazolinylurea | 0.30 g |
| Kathon CG | 0.05 g |
| Disodium EDTA | 0.10 g |
| PEG-5 soy sterols (Generol 122 E5 - Henkel) | 2.00 g |
| Octyldodecanol (Eutanol G - Henkel) | 4.00 g |
| Wheat germ oil | 4.00 g |
| Silicone oil 350 cps | 0.50 g |
| Glycerylstearate (Cutine GMS - Henkel) | 7.00 g |
| Polysorbate 60 (Tween 60 - ICI) | 5.00 g |
| Tocopherol | 0.20 g |
| Ascorbyl palmitate | 0.10 g |
| 10% NaOH solution | 2.00 g |
| Perfume (186909 - Dragoco) | 0.20 g |
| Purified water | up to 100.00 g |

Example 8

Formulation Containing a *Ferula hermonis* Pure Extract with a Ferutinine Content of 30% and a jaeschkenadiol benzoic ester Content of 20%

| | |
|---|---|
| *Ferula hermonis* extract | 0.5 g |
| Carbomer 934 (Carbopol 934 P - Goodrich) | 0.60 g |
| Propylene glycol | 3.00 g |
| Imidazolinylurea | 0.30 g |
| Kathon CG | 0.05 g |
| Disodium EDTA | 0.10 g |
| PEG-5 soy sterols (Generol 122 E5 - Henkel) | 2.00 g |
| Octyldodecanol (Eutanol G - Henkel) | 4.00 g |
| Wheat germ oil | 4.00 g |
| Silicone oil 350 cps | 0.50 g |
| Glycerylstearate (Cutine GMS - Henkel) | 7.00 g |
| Polysorbate 60 (Tween 60 - ICI) | 5.00 g |
| Tocopherol | 0.20 g |
| Ascorbyl palmitate | 0.10 g |
| 10% NaOH solution | 2.00 g |
| Perfume (186909 - Dragoco) | 0.20 g |
| Purified water | up to 100.00 g |

Example 9

Gel Containing Ferutinine

| | |
|---|---|
| Ferutinine | 0.30 g |
| Imidazolinylurea | 0.30 g |
| Methylparaben | 0.20 g |
| Hydroxyethylcellulose (Natrosol 250 HHX - Aqualon) | 2.00 g |
| Purified water | up to 100 ml |

Example 10

Cosmetic Formulation Containing *Ferula* spp Extract

| | |
|---|---|
| *Ferula hermonis* extract | 0.5 g |
| Imidazolinylurea | 0.30 g |
| Methylparaben | 0.20 g |
| Hydroxyethylcellulose (Natrosol 250 HHX - Aqualon) | 2.00 g |
| Purified water | up to 100 ml |

EXPERIMENTATION

Product Effectiveness

The effectiveness of the cream of example 7 was determined in a double blind study with 40 female volunteers, of age ranging from 39 to 56, evaluating the effects on skin elasticity and firmness and on rugometry. The study was preceded by a seven days conditioning period, wherein the subject had to refrain from the use of moisturizing products, sun-creams and liquid make-ups and to avoid tanning treatments and excessive exposition to UV rays.

The subjects were allowed to use conventional eye and lip care products, face powders and non moisturizing soaps.

The subjects were randomly divided into two groups, one treated with a placebo cream and one treated with the cream of example 7. The creams were applied on the face in standardized amount (0.5 g, i.e. 0.5 cm of cream coming out of the tube) twice a day, morning and night. Before and after five weeks of treatment the following measurements were carried out.

Before each measurement session all the subjects stayed for thirty minutes in a climatic chamber at 23° C. and 50% of relative humidity. Each session comprised three measurements with corneometer, three measurements with cutometer, and a silicon impression of the periorbital area, on the skin areas indicated in the following.

All the 40 subjects completed the study.

Cutometry

Cutometer is a commercially available device (Cutometer SEM 575, Courage & Khazaka, Germany) for measuring skin mechanical properties in a non-invasive way. In more detail, it measures the vertical deformation of the skin surface when subjected to a negative pressure of 500 mm Hg through a 2 mm opening of a probe. The length of skin penetration in the probe is optically measured with 0.01 mm precision. The probe is connected with a computer that registers skin deformation over time. From the resulting curve, numerous variables can be extrapolated to evaluate skin elastic, viscoelastic and viscous behaviour.

The following parametres were recorded:
immediate distension (Ue), measured at 0.1 seconds;
delayed distension (Uv);
final distension (Uf), measured at 10 seconds; and
immediate retraction (Ur).

The test was carried out using the cutometer on both cheeks.

Significant variations were not observed in the placebo group. Delayed distention (Uv) in the treated group significantly decreased (16%, $p<0.05$) after 5 weeks treatment. This parameter reflects skin viscoelastic properties and dermis behaviour. After 5 weeks, a significant change was also observed ($-12\%$, $p<0.05$) in Ue, which is mainly influenced by hydration and mechanic properties of the corneum layer. The decrease in Uv and Ue, together with Ur stability, shows increased skin firmness.

Corneometry

Soft and smooth skin appearance mostly depends on the presence of an adequate amount of water in the corneous layer.

Corneometer is a commercially available device (Corneometer CM 825 Combi 3, Courage & Khazaka, Germany) which measures capacitance changes resulting from changes in skin hydration.

The test was carried out using the corneometer on both cheeks.

After 5 weeks, a significant change in the treated group was observed, in particular, skin hydration increased by 17.5%, while in the placebo group it decreased by 3%.

Rugometry

Silicon impressions were carried out on subjects in the seated position. The impressions (2×5 cm) were obtained at the beginning and after 5 weeks, using "Silflo silicon impression material" (available from Flexico, UK).

The impressions were then analysed with the Skin Image Analyzer system using the Quantirides—Monaderm software, which distinguishes cutaneous microrelief from median wrinkles and deep wrinkles and calculate their number and depth; finally, the value of total wrinkle area is obtained.

After 5 weeks, significant changes were observed in the treated group. In particular, a 21.3% ($p<0.05$) decrease in the wrinkle area was observed, whereas in the placebo group the decrease was 0.4%.

Statistically significant decrease has been observed mainly in the number and depth of median and deep wrinkles.

CONCLUSION

The study allowed to conclude that the cream of example 7 has good cosmetic activity in the treatment of skin with chrono- and photoaging signs, as it increases skin firmness and hydration and decreases mean wrinkled area, in particular deep micro- and macrorugosities. Skin visibly appeared firmer and smoother.

What is claimed is:

1. A method of reducing wrinkles in a patient in need thereof, consisting essentially of:
    applying onto the patient's skin a composition consisting essentially of a therapeutically effective amount of ferutinine.

2. A method of reducing wrinkles in a patient in need thereof, consisting essentially of:
    applying onto the patient's skin a composition consisting essentially of a therapeutically effective amount of ferutinine and an excipient selected from the group consisting of soy lecithin, phospholipids, lauroylphosphatidylcoline and myristoylphosphatidilcoline.

3. The method according to claim 1, wherein the composition is in a form selected from the group consisting of an emulsion, a transdermal plaster, a cream, a gel and a lotion.

4. The method according to claim 2, wherein the composition is in a form selected from the group consisting of an emulsion, a transdermal plaster, a cream, a gel and a lotion.

* * * * *